United States Patent
Knowles

(10) Patent No.: US 6,921,363 B2
(45) Date of Patent: Jul. 26, 2005

(54) TRANSESOPHAGEAL ENDOSCOPE WITH IMPROVED BITE-THROUGH PROTECTION

(75) Inventor: Heather Beck Knowles, Devens, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/264,600

(22) Filed: Oct. 3, 2002

(65) Prior Publication Data

US 2004/0068183 A1 Apr. 8, 2004

(51) Int. Cl.$^7$ .................................................. A61B 1/00
(52) U.S. Cl. ....................................... 600/139; 600/140
(58) Field of Search ............................... 600/139, 140, 600/141, 142, 562, 570; 606/1

(56) References Cited

U.S. PATENT DOCUMENTS

| 5,020,539 | A | * | 6/1991 | Yokoi et al. ................ 600/116 |
|---|---|---|---|---|
| 5,156,155 | A | | 10/1992 | King |
| 5,388,584 | A | | 2/1995 | King |
| 5,439,454 | A | * | 8/1995 | Lo et al. ..................... 604/264 |
| 5,749,828 | A | | 5/1998 | Solomon et al. |
| 5,885,209 | A | * | 3/1999 | Green ......................... 600/153 |
| 6,262,329 | B1 | * | 7/2001 | Brunsveld et al. ............ 602/54 |
| 6,321,794 | B1 | * | 11/2001 | Ishida et al. ................ 138/121 |
| 6,458,075 | B1 | * | 10/2002 | Sugiyama et al. .......... 600/139 |
| 6,540,669 | B2 | * | 4/2003 | Abe et al. ................... 600/140 |
| 6,565,507 | B2 | * | 5/2003 | Kamata et al. ............. 600/153 |
| 2002/0100516 | A1 | * | 8/2002 | Powell et al. .............. 138/125 |

* cited by examiner

Primary Examiner—Beverly M. Flanagan
(74) Attorney, Agent, or Firm—W. Brinton Yorks, Jr.

(57) ABSTRACT

A transesophageal probe shaft has a cover which is formed by a plurality of separate layers joined by a pressure sensitive adhesive. In a preferred embodiment the cover forms the outer cover of an articulating section of the probe. The layers are chosen to be thin enough so that the stiffness of the cover does not significantly restrain the bending of the articulating section. The adhesive viscosity is chosen to enable the joined layers to be able to move relative to each other as the probe is bent, and to be able to flow to fill any small cut in the cover caused by biting through the cover.

18 Claims, 4 Drawing Sheets

FIG. 1 *(Prior Art)*
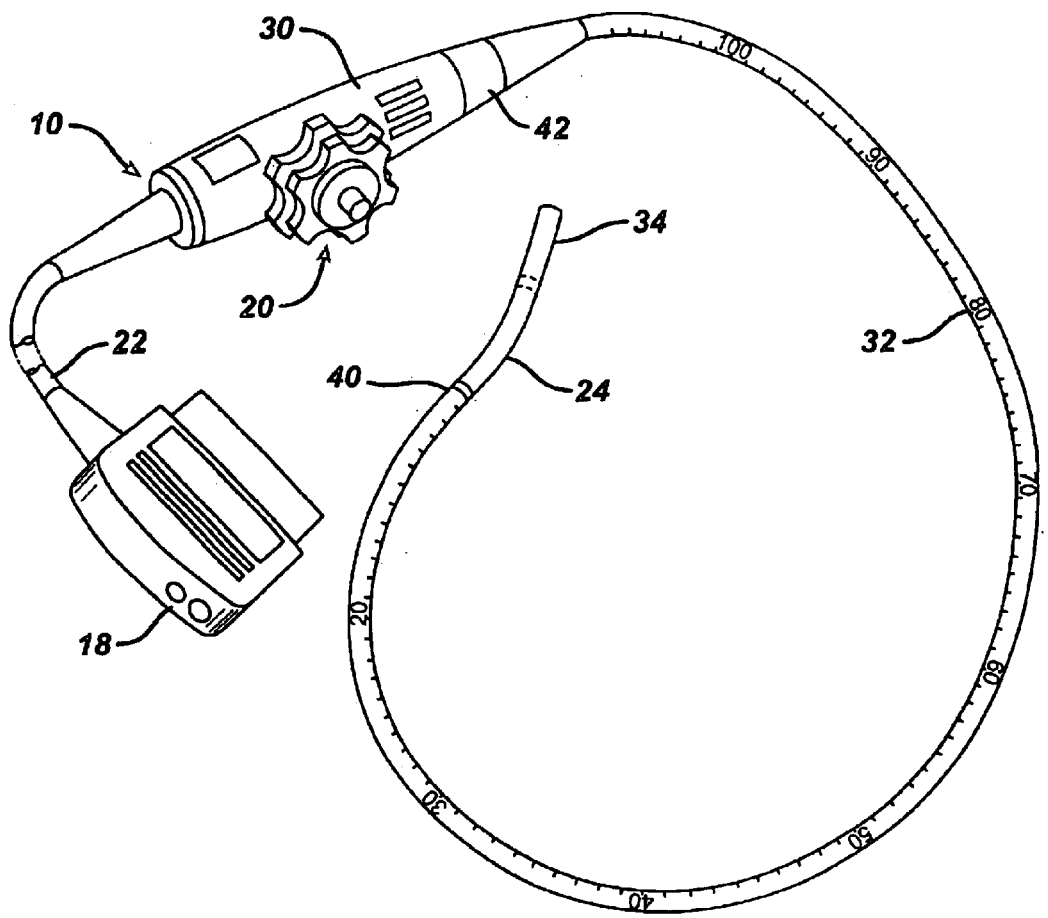
FIG. 2 *(Prior Art)*
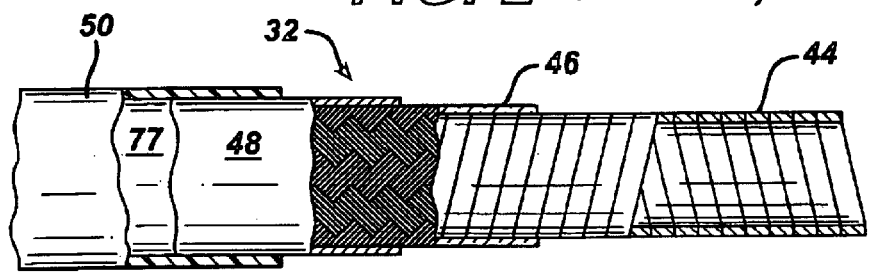

TRANSESOPHAGEAL ENDOSCOPE WITH IMPROVED BITE-THROUGH PROTECTION

This invention relates to transesophageal endoscopes and, in particular, to ultrasonic transesophageal echocardiography (TEE) probes with bite-through protection.

Ultrasonic TEE probes have been in widespread use for over a decade for cardiac diagnosis and monitoring. An ultrasonic TEE probe is a gastroscope with an ultrasonic transducer at the distal tip. The tip is inserted down the esophagus and sometimes into the stomach from which the transducer scans the heart for diagnostic imaging or monitoring purposes. The transducer is moved while in the body by a short articulation section preceding the tip which is controlled from a handle outside the body. A diagnostic TEE probe produces cardiac images which do not have to contend with the chest wall, ribs, or lungs as transthoracic probes do. Rather than having to transmit and receive ultrasound from between the ribs, the TEE probe has direct access to the heart from the esophagus or stomach, unimpeded by the ribs.

The TEE probe is used by inserting the gastroscope down the throat of the patient. Although insertion of the probe is usually proceeded by the spraying of a topical anesthetic in the throat, insertion of the probe usually provokes a choking response, whereby the patient will reflexively bite down on the probe entering his mouth. The biting of the probe can cut or damage the probe. Bite guards are sometimes used to prevent this problem, but they can become dislodged or even bitten through. A severe bite on the probe can damage the internal components of the probe, can expose the patient to electrical hazard, or will allow the ingress of gastric fluids, reducing the ability to fully sterilize the probe between uses. Accordingly it is desirable for a TEE probe to be resistant to biting so that cuts through the cover of the probe are prevented and the patient protected from electrical hazards.

In accordance with the principles of the present invention a cover for the articulating section of a TEE probe is provided. The cover comprises two or more layers, including an inner sheath and an outer sheath, with a viscous adhesive therebetween. The sheaths are formed from a tough, flexible polymer which is sufficiently thin to enable the articulating section to bend freely. The two layer composition has been found to be more greatly resistant to bite-through than a single layer construction of the same thickness. The viscous adhesive allows the two sheaths to move relative to each other, and will flow to seal any openings in the sheaths caused by biting. The composite structure is an electrical dielectric which isolates the patient from electrical hazards.

In the drawings:

FIG. 1 is a pictorial representation of a transesophageal probe utilizing an articulating tip in accordance with the principles of the present invention;

FIG. 2 is a partially cutaway, cross-sectional side view of a probe shaft;

Figure 3A:
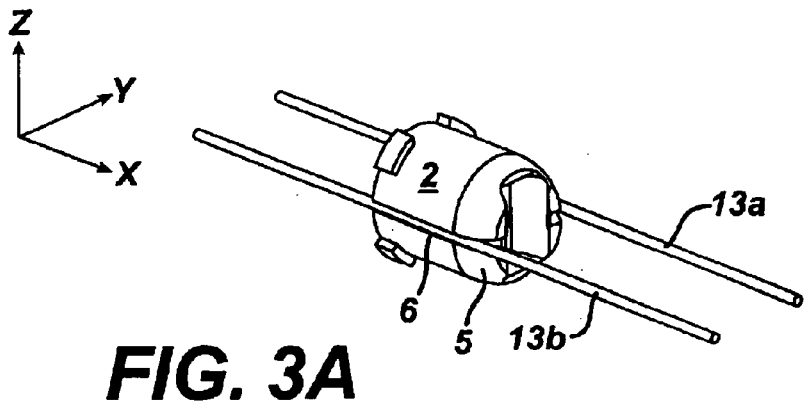

FIGS. 3A–3E FIG. 4 is a cross-sectional view of a probe articulating section and cover constructed in accordance with the principles of the present invention.

With reference now to the drawings, and more particularly to FIG. 1 thereof, there is shown a pictorial representation of a typical transesophageal probe 10 with which the articulating section of the present invention is to be used. Probe 10 is an ultrasonic probe suitable for insertion into a particular body cavity or orifice, namely the esophagus or the mouth. It is to be understood that this invention is being described with reference to a transesophageal probe for purposes of illustration only, and that this invention has equal applicability to other invasive bodily probes which utilize an articulating section which must be protected from damage, and which must be electrically insulated from the patient, such as transrectal, transnasal and endoscopic probes.

Probe 10 includes a proximal handle portion 30, a distal tip portion 34, a somewhat flexible shaft 32 connecting handle portion 30 with distal tip portion 34 and electrical connector 18. Shaft 32 is connected to a flexible section 24 adjacent distal tip portion 34 which can be bent. Distal tip portion 34 typically includes a transducer (not shown), and electrical cables 22 travel from connector 18, through handle portion 30 and shaft 32 to the transducer. Distal tip portion 34 can be deflected for proper positioning of the transducer by bending of section 24. This deflection is produced by rotation of wheels 20 which are mechanically coupled to portion 24 by cables or other mechanisms which extend through shaft 32. The details of the structure of transesophageal probe 10 are well know to those skilled in the art, and need not be further discussed herein.

During use of the transesophageal probe 10, distal tip portion 34 is inserted into the patient's mouth and down his esophagus to be positioned therein or in the stomach for scanning of the heart or other bodily organs. During this process, some abrasion of the outer surface of flexible section 24 and shaft 32 can occur, and the patient could inadvertently bite down on shaft 32 or flexible section 24 during the process. Should a patient puncture the outer coating of the shaft or flexible section, he could become electrically connected to the electrical cables passing from connector 18 to distal tip 14, or to other electrically conductive elements of the probe. Furthermore, gastric fluids and the like could penetrate a puncture and enter the interior of the probe, thus possibly damaging the mechanical and electrical cables and other components passing therethrough and rendering the probe difficult to properly sterilize or possibly inoperable due to internal electrical shorting.

To prevent these hazards, the shaft 32 can be constructed as shown in FIG. 2. Shaft 32 extends between connections 40 and 42. Shaft 32 includes an inner convoluted core 44, a stainless steel sheath 46 surrounding core 44, a membrane 48 surrounding sheath 46 and an outer, tough, elastomeric coating 50 covering membrane 48. Core 44 typically is composed of stainless steel, while sheath 46 typically is formed of braided stainless steel. However, it is to be understood that core 44 may be composed of other materials besides stainless steel, so long as the required strength, rigidity and structural support are provided to prevent crushing of the core. Similarly, while a stainless steel braid is preferred for sheath 46, another similarly corrosion resistant, strong, durable material could be used. Also, while an elastomeric material is preferred for coating 50, other equally durable, corrosion resistant, dielectric materials could be utilized. Further details of this shaft construction may be found in U.S. Pat. No. 5,388,584.

The bending or articulating section 24 may be constructed as shown in FIGS. 3A–3E. The section articulates by means of a bending neck formed by a series of links. FIGS. 3A–3E show an assembly sequence of a portion of a typical bending neck. A series of the cascading links 2 and sleeves 12 are used in the construction of the bending neck. Each link has a tapered ball end 5 and an opposite open socket end 3. In FIG. 3A, cables 13a, 13b are shown inserted in each of the diametrically opposed channels 6 of the link 2. A constructed embodiment may have two, three, or four control cables spaced uniformly about the circumference of the bending neck. These cables convey the turning of wheels 20 to the bending neck, causing the neck to bend in a direction desired to properly place the transducer tip adjacent the structure to be imaged. In a preferred embodiment four cables are used. For ease of illustration only two cables are shown in FIGS. 3A–3E.

Figure 3B:
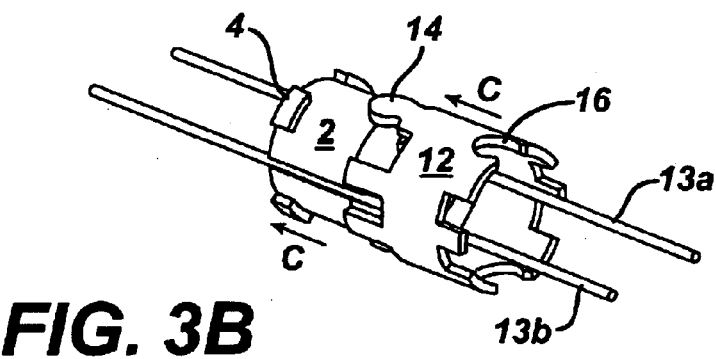
Figure 3C:
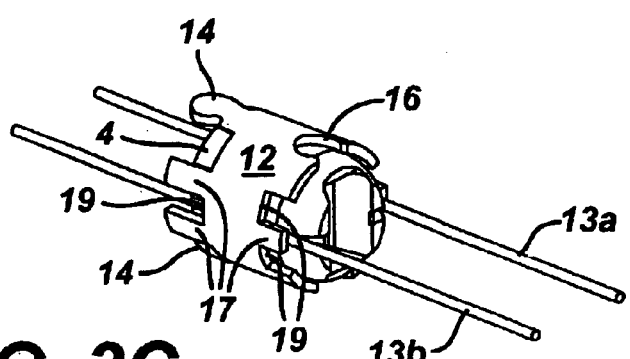

FIGS. 3B–3C show the sleeve 12 positioned to slide over the link 2. The sleeve 12 is threaded over the end of the cables 13a and 13b and moved in the direction indicated by the arrows C. Once the sleeve 12 is in place, it is engaged and held in place by the tabs 4. The sleeve 12 captively holds the cables 13a and 13b in the channels 6 of the link 2. The pair of diametrically opposed swivel joints 14 at one end of the sleeve 12 is rotationally offset by 90° relative to the channels 6 and the cables 13a and 13b. At the other end of the sleeve 12, the pair of swivel sockets 16 are adapted to receive a corresponding pair of swivel joints 14.

Figure 3D:
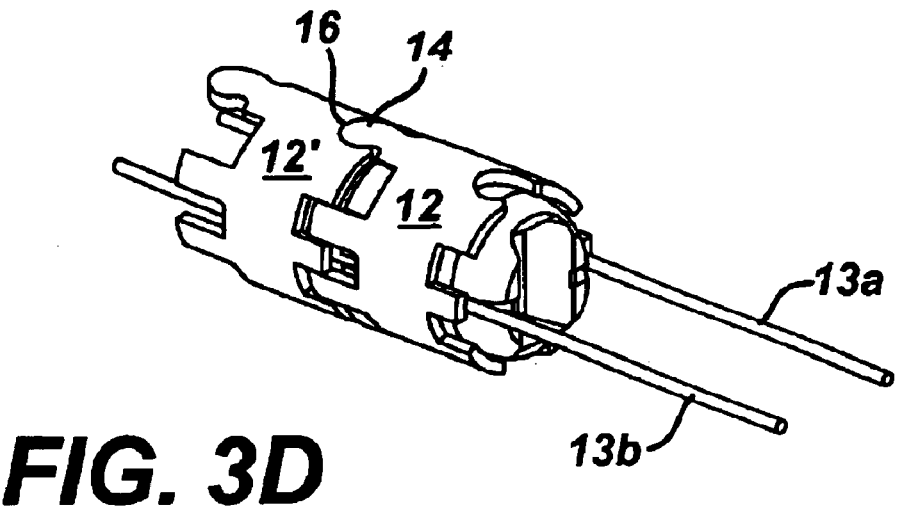

In FIG. 3D a second sleeve 12' is shown pivotally attached to an adjacent sleeve 12. To install the second sleeve 12', it is first threaded over the end of the cables 13a and 13b and is slid next to the adjacent sleeve 12, oriented with the swivel socket 16 of the second sleeve 12' facing the swivel joint 14 of the first sleeve 12. Initially the second sleeve 12' is offset in the Z-axis direction relative to the first sleeve 12. Once the swivel sockets 16 of the second sleeve 12' are aligned with the swivel joints 14 of the first sleeve 12, the second sleeve 12' is moved in the -Z direction to eliminate the offset, such that the swivel joints 14 are captively held by the swivel sockets 16, and the first sleeve 12 and the second sleeve 12' are in coaxial alignment.

Figure 3E:
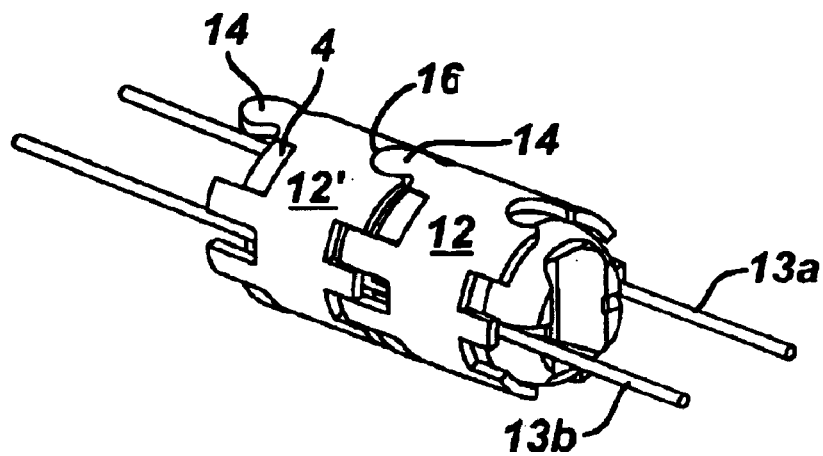

As shown in FIG. 3E, a second link 2' is inserted in the second sleeve 12' and also engaged by tabs 4. Although the second link 2' is not visible in FIGS. 3D and 3E, the tapered ball end 5 of the second link 2' is inserted into the open socket end of the first link 2. As with the first link 2, the second link 2' also has the cables 13 guided through the channels 6 and the cables 13 are captively held within the channels 6 by the sleeves 12. Successive sleeves 12 and links 2 are added in an identical sequence, a sleeve 12 with its swivel socket 16 adjacent to the preceding sleeve's 12 swivel joint 14, followed by the insertion of a corresponding link 2 inside the sleeve 12 with the ball 5 of one link 2 inserted into the socket 3 of the preceding link 2, until the desired number of sleeve 12 and link 2 pairs, or segments is attained. The number of segments is determined by the length of the bending neck needed in a particular application. Further details on the fabrication and assembly of the bending neck may be found in U.S. Pat. No. 5,749,828.

Figure 4:
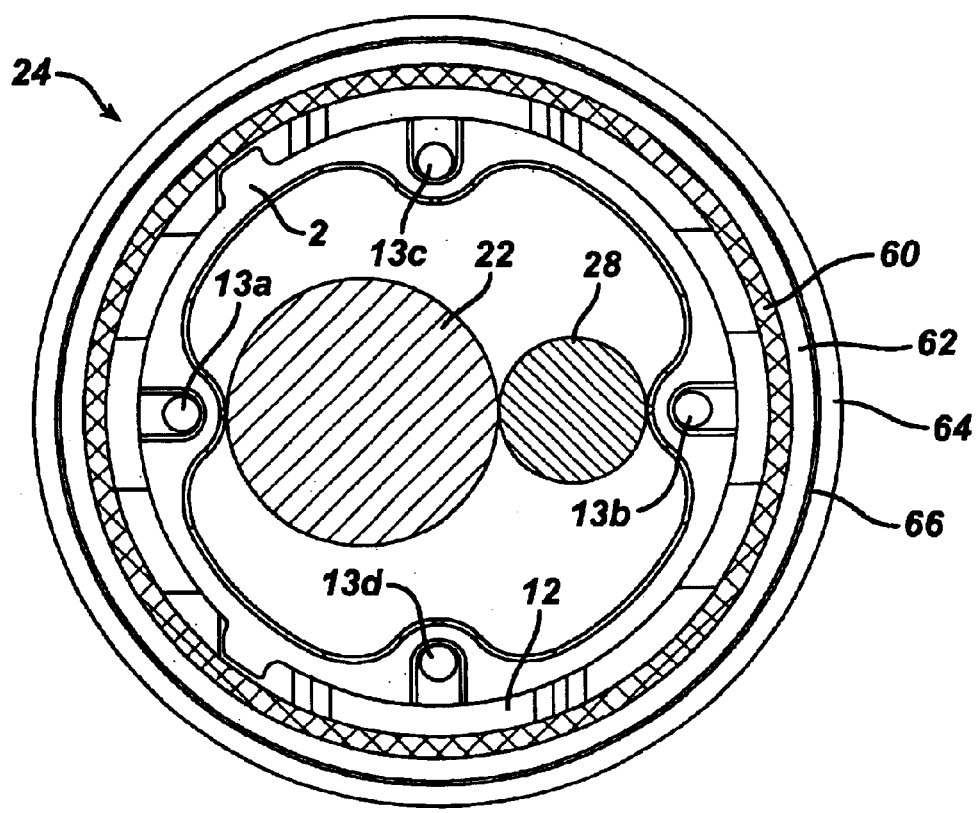

In accordance with the principles of the present invention, the bending neck is covered with a flexible dielectric cover which resists bite-through damage as shown in FIG. 4. FIG. 4 is a cross-sectional view of the assembled articulating section 24. Located inside the core of the links 2 and sleeves 12 are the electrical cables 22 which extend from the connector 18 to the transducer in the distal tip 34. In an ultrasonic transesophageal probe for cardiac applications the transducer is generally a multi-element phased array transducer. The electrical cables connect the elements of the transducer to connecting pins in the connector 18, and may comprise multiple coaxial conductors or multi-conductor flex circuit. In the illustrated embodiment the transducer can be rotated by the user to rotate the scan plane to a desired position. Such omni-directional transducer TEE probes are described in U.S. Pat. No. 4,543,960, for example. The transducer can be rotated by a manually controlled mechanism as described in the '960 patent, or under automated control as described in U.S. Pat. No. 5,181,514, which describes the use of a motor in the handle portion 30 with a drive shaft extending to a rotationally mounted transducer in the distal tip 34. The illustrated embodiment utilizes such a motor arrangement, with a transducer drive shaft 28 extending through the shaft and articulating section of the probe. An alternative arrangement has the transducer mounted to a tiny motor located in the distal tip, in which case only electrical connections to the motor would extend through the shaft and articulating section.

In accordance with the principles of the present invention, the bending neck is enclosed by a polymer braid 60. The polymer braid can be a woven, knitted, or non-woven textile, although a woven textile is preferred. This layer can be formed of polyaramid, cotton, wool, polyester, Nylon®, or polypropylene fibers. The preferred material is a polymer such as Nylon or Dacron®. The polymer braid serves to prevent the bending neck from cutting or engaging the surrounding protective cover and provides an additional measure of cut-through protection by virtue of the compliance it provides for the overlaying cover materials. Surrounding the polymer braid is a two-layer sheath with pressure sensitive adhesive 66 located between the two layers. The layers 62, 64 can be form from various elastomeric materials such as urethane, thermoplastic elastomers, fluoropolymers, or neoprene. In a preferred embodiment the layers 62, 64 are each formed by a tube of fluoropolymer, and the adhesive is a pressure sensitive or contact adhesive available from the 3M Company such as a 300 series or 400 series pressure sensitive adhesive. The sheath is formed by a molding technique. The two tubes are substantially the same diameter. The tube which is to be used as the inner layer 62 is placed over the braid 60 and coated with the pressure sensitive adhesive. While the adhesive may be spread onto the tube and then allowed to cure, preferably the adhesive is a pressure sensitive adhesive located on transfer tape and transferred from the tape to the inner tube. The tube which is to be the outer layer is expanded by being drawn in a vacuum as described in the '584 patent, and the expanded outer tube is slipped over the adhesive coated inner tube and the vacuum released. Connections may then be applied to the ends of the bending neck to connect the flexible section to the shaft 32 and the distal tip 34.

The articulating section cover of two thin polymeric layers with an intermediate adhesive has been found to provide the desired complement of flexibility for the bending neck as well as high bite-through protection. The adhesive does not cure to a hard substance, but remains pliant. As such, it does not rigidly join the two polymeric layers 62, 64 together, but allows them to move slightly relative to each other as the articulating section bends. The relative motion causes the cover to provide relatively low resistance to bending. The user does not feel that he is overcoming a bending-resistant cover while articulating the neck.

The two-layer construction also provides good cut-through resistance. It has been found that the cut-through resistance of a cover layer increases linearly with increases in thickness. At the same time, stiffness of the layer increases by the third power as the thickness increases. Furthermore, it has been found that cut-through resistance can be increased by a factor of ten by separating one thick layer into two thinner layers. A test fixture was constructed with a blade which was repeatedly pressed into a cover of a probe of the present invention and into a cover of a prior art probe with a known force. It was found that a 30 mil sheath would resist cut-through for approximately 30–40 cycles. A sheath formed of two 15 mil layers was found to resist cut-through for approximately 400 cycles. This combination of parameters shows that a probe cover formed of multiple thin layers as is the cover of the present invention will be more flexible than a single layer cover of the same thickness and will provide better resistance to bite-through.

In addition to allowing the two layers of the cover to move relative to each other as the articulating section bends, the viscoelastic adhesive responds to cuts in the cover by pulling the edges of a cut layer back toward each other, thereby closing holes in the cover. It has been found that this sealing effect is fluid-tight, which prevents the ingress of gastric fluids into the core of the probe as it is used, thereby preventing the development of electrical hazards. Since the adhesive is a dielectric, the patient remains electrically insulated from the electrical components and elements in the core of the neck. This is an improvement over use of a braided metal sheath for bite-through protection, which must be grounded to prevent its behavior as an antenna which can introduce electrical interference into the probe. To prevent this antenna effect, the metal braid must be grounded, but connecting the braid to the electrical system of an ultrasound system can present an electrical hazard to the patient when the cover is cut through to the braid. The cover of the present invention, needing no metal braid, obviates these difficulties.

The inventive cover is an improvement over sandwiched textile designs due to its decreased diameter which increases patient comfort, and its improved reliability.

One skilled in the art will recognize that the inventive cover describe above can be used for the articulating section cover, the shaft cover, or both.

What is claimed is:

1. A shaft for use with a probe adapted to invade a bodily cavity, the shaft comprising:
    an inner core providing a passage for probe components; and
    a multi-layer cover enclosing the inner core, the cover including an inner polymeric layer and an outer polymeric layer joined by an intermediate layer of a pliant adhesive.

2. The shaft of claim 1, wherein the inner core further comprises an articulating neck.

3. The shaft of claim 1, wherein the polymeric layers comprise fluoropolymer layers.

4. A shaft for use with a probe adapted to invade a bodily cavity, the shaft comprising:
    an inner core providing a passage for probe components; and
    a multi-layer cover enclosing the inner core, the cover including an inner polymeric layer and an outer polymeric layer joined by an intermediate adhesive layer,
    wherein the adhesive layer is a viscous adhesive layer.

5. The shaft of claim 4, wherein the viscosity of the adhesive layer is chosen so that the adhesive allows at least some relative movement between the inner and outer polymeric layers as the shaft is bent.

6. The shaft of claim 4, wherein the viscosity of the adhesive layer is chosen so that the adhesive will exhibit a tendency to close a small cut occurring in the outer polymeric layer.

7. A shaft for use with a probe adapted to invade a bodily cavity, the shaft comprising:
    an inner core providing a passage for probe components; and
    a multi-layer cover enclosing the inner core, the cover including an inner polymeric layer and an outer polymeric layer joined by an intermediate adhesive layer,
    wherein the adhesive layer is formed by a contact adhesive.

8. An ultrasonic probe for use inside a body cavity comprising:
    a distal tip portion containing a transducer;
    an articulating section coupled to the distal tip portion;
    a handle portion containing a mechanism which controls the articulating section;
    a shaft coupled between the articulating section and the handle portion; and
    a cover, located between the distal tip and the handle portion and covering an indwelling section of the probe, comprising a first outer polymeric layer, a second inner polymeric layer, and a pressure sensitive adhesive located between the outer and inner polymeric layers.

9. The ultrasonic probe of claim 8, wherein the indwelling section of the probe comprises the articulating section.

10. The ultrasonic probe of claim 9, wherein the articulating section comprises a plurality of links connected to form a controllably articulating section.

11. The ultrasonic probe of claim 10, wherein the thicknesses of the outer and inner polymeric layers are chosen to enable the articulating section to be articulated without significant resistance from the stiffness of the cover.

12. The ultrasonic probe of claim 8, wherein the indwelling section of the probe comprises the shaft section.

13. The ultrasonic probe of claim 8, wherein the pressure sensitive adhesive exhibits a viscosity which enables at least some relative movement between the outer and inner layers.

14. The ultrasonic probe of claim 8, wherein the pressure sensitive adhesive exhibits a tendency to close a small cut in the outer layer.

15. The ultrasonic probe of claim 14, wherein the pressure sensitive adhesive exhibits a viscosity which enables the adhesive to exhibit a tendency to close a small cut extending through the inner and outer layers.

16. The ultrasonic probe of claim 14, wherein the small cut is caused by biting.

17. The ultrasonic probe of claim 8, further comprising a braided polymer layer located inside the inner polymer layer.

18. The ultrasonic probe of claim 8, wherein the inner and outer polymeric layers comprise fluoropolymeric layers.

* * * * *